United States Patent [19]

Siegel et al.

[11] Patent Number: 4,749,524

[45] Date of Patent: Jun. 7, 1988

[54] PROCESS FOR THE PREPARATION OF 2-CHLOROETHANEPHOSPHONIC DICHLORIDE

[75] Inventors: Herbert Siegel; Erwin Weiss, both of Hofheim am Taunus; Harald Berger, Kelkheim, all of Fed. Rep. of Germany

[73] Assignee: Hoechst Aktiengesellschaft, Frankfurt am Main, Fed. Rep. of Germany

[21] Appl. No.: 89,827

[22] Filed: Aug. 27, 1987

[30] Foreign Application Priority Data

Aug. 30, 1986 [DE] Fed. Rep. of Germany ....... 3629579

[51] Int. Cl.$^4$ .................................................. C07F 9/42
[52] U.S. Cl. ........................... 260/543 P; 260/502.4 R
[58] Field of Search ...................................... 260/543 P

[56] References Cited

U.S. PATENT DOCUMENTS 3,890,382 6/1975 Hofer et al. ..................... 260/543 P

FOREIGN PATENT DOCUMENTS 764873 3/1971 Belgium ........................... 260/543 P 582259 11/1977 U.S.S.R. ........................... 260/543 P Primary Examiner—Paul J. Killos

[57] ABSTRACT

The invention relates to a process for the preparation of 2-chloroethanephosphonic dichloride through reaction of a 2-chloroethanephosphonate of the formula

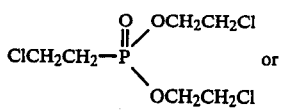

or

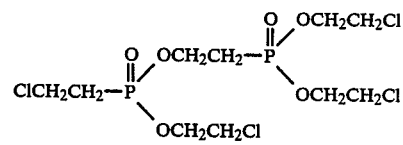

or a mixture of the two esters, with thionyl chloride at a temperature of 60° to 160° C. In this reaction, tertiary phosphines, quaternary ammonium or phosphonium salts or alkali metal or alkaline-earth metal halides are employed as catalysts. The thionyl chloride is introduced into the initially introduced ester.

8 Claims, No Drawings

PROCESS FOR THE PREPARATION OF 2-CHLOROETHANEPHOSPHONIC DICHLORIDE

The invention relates to a process for the preparation of 2-chloroethanephosphonic dichloride through reaction of a 2-chloroethanephosphonate of the formula

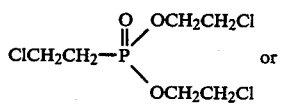

or

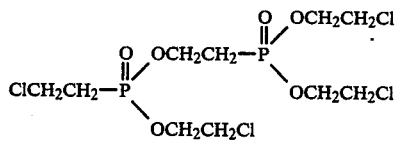

or a mixture of the two esters, with thionyl chloride at a temperature of 60° to 160° C.

2-Chloroethanephosphonic dichloride

is a valuable intermediate. Through hydrolysis, 2-chloroethanephosphonic acid is obtained, which is important as a plant-growth accelerator. Through reaction with hydroxyalkyl or mercaptoalkyl compounds, phosphonates or thiophosphonates are obtained. Such compounds are used as flameproofing agents or as plant-protection agents. Furthermore, through elimination of HCl from 2-chloroethanephosphonic dichloride, vinylphosphonic dichloride can be prepared (Swiss Pat. No. 391,699 and German Offenlegungsschrift No. 1,568,945), which can itself be hydrolyzed to form vinylphosphonic acid. This is an important intermediate in the preparation of flameproofing agents. In addition, it is an important monomer in the preparation of homo- or copolymers. Such polymers are important in paints, plastics, corrosion inhibitors and coating agents.

U.S. Pat. No. 4,213,922 discloses that 2-chloroethanephosphonic dichloride can be prepared from the above-mentioned bis-2-chloroethyl 2-chloroethanephosphonates with the aid of thionyl chloride. In this reaction, tertiary amines, N,N-disubstituted formamides or N,N-disubstituted phosphoric triamides are employed as catalysts. However, in spite of long reaction times, the yield is extremely low, as shown by Example 4 in this literature citation.

German Offenlegungsschrift No. 2,132,962 discloses the same reaction with the aid of phosgene in place of thionyl chloride. In this reaction, tertiary phosphines and quaternary ammonium or phosphonium salts, inter alia, are employed as catalysts. These catalysts were already the state of the art on the priority date of U.S. Pat. No. 4,213,922; however, they are not used in processes according to the U.S. patent. Obviously, the presence of tertiary phosphines or quaternary ammonium or phosphonium salts was not regarded as favorable when thionyl chloride is used. This is because it is known, for example, that tertiary phosphines undergo a number of reactions with thionyl chloride and $SO_2$ which would interfere in the present case (Chemical Abstracts, Vol. 77, 1972, 48575 h and J. Chem. Soc. 1965, 5516).

Surprisingly, it has now been found that 2-chloroethanephosphonic dichloride can be prepared in a short reaction time and in high yields from the 2-chloroethanephosphonates mentioned with the aid of thionyl chloride in the presence of the catalysts mentioned or alternatively in the presence of alkali metal or alkaline-earth metal halides.

The invention therefore relates to a process for the preparation of 2-chloroethanephosphonic dichloride through reaction of a 2-chloroethanephosphonate of the formula

or

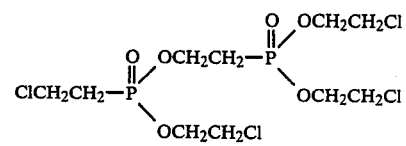

or a mixture of the two esters, with thionyl chloride at a temperature of 60° to 160° C., wherein the reaction is carried out in the presence of a catalyst which contains at least one of the following substances:

(a) tertiary phosphines of the general formula

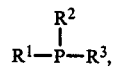

in which the radicals $R^1$, $R^2$ and $R^3$ may be identical or different and denote straight-chain or branched $C_1-C_{10}$-alkyl, optionally substituted by $C_1-C_4$-alkoxy, $C_1-C_4$-alkylthio or $C_1-C_4$-dialkylamino radicals, or denote phenyl, optionally substituted by halogen, $C_1-C_4$-alkyl or $C_1-C_4$-alkoxy radicals, (b) quaternary ammonium or phosphonium salts of the general formula

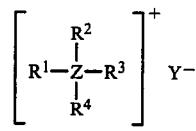

where $Z=N$ or $P$, where $Y^-$ is an anion of a strong acid and in which $R^1$, $R^2$ and $R^3$ have the meaning mentioned in the case of (a) and $R^4$ denotes straight-chain or branched $C_1-C_{10}$-alkyl, or benzyl which is substituted by halogen, $C_1-C_4$-alkyl or $C_1-C_4$-alkoxy radicals, (c) alkali metal or alkaline-earth metal halides.

$R^1$, $R^2$ and $R^3$ are preferably $C_1-C_4$-alkyl radicals (optionally substituted as specified above) or phenyl radicals (optionally substituted in the abovementioned fashion). $R^4$ is preferably a $C_1-C_4$-alkyl radical, or benzyl which is substituted by halogen, $C_1-C_4$-alkyl or $C_1-C_4$-alkoxy radicals.

The reaction temperature is 60°-160° C., preferably 60°-140° C. in particular 80°-130° C. The thionyl chloride:ester employed molar ratio is 2:1 to 4:1, preferably 2.5:1 to 3.5:1. The amount of catalyst is 0.1 to 10 mole-percent, preferably 0.5 to 2 mole percent relative to the ester employed.

A catalyst which contains at least one of the tertiary phosphines mentioned under (a) or the metal halides mentioned under (c) is preferably used. The following tertiary phosphines are particularly suitable: triphenyl phosphine, tris(4-fluorophenyl) phosphine, tris(4-tolyl) phosphine, tris(4-methoxyphenyl) phosphine, (N,N-diethyl)aminomethyldiphenyl phosphine, tri-n-butyl phosphine and bis(4-methoxyphenyl)methyl phosphine. Triphenyl phosphine is very particularly suitable.

Amongst the metal halides according to (c), lithium bromide is particularly suitable.

Suitable anions $Y^-$ of a strong acid in the formula for the quaternary ammonium or phosphonium salts are, for example, $Cl^-$, $Br^-$, $I^-$, $NO_3^-$, $SO_4^-$, $HSO_4^-$ and $PO_4^-$, i.e. the symbol $Y^-$ shall also represent polyvalent anions.

If quaternary ammonium and phosphonium salts are employed as catalysts, those are particularly suitable which are used in phase-transfer catalysis, for example tetrabutylammonium bromide, tetrabutylphosphonium bromide, tetrabutylammonium hydrogen sulfate, methyltrioctylammonium chloride, benzyltrimethylammonium bromide, and benzyltriethylammonium chloride, but above all tetrabutylammonium bromide and tetrabutylphosphonium bro- mide.

In order to ensure a sufficient reaction time for the relatively inert phosphonates, the thionyl chloride is preferably introduced into the initially introduced ester. The thionyl chloride is particularly preferably introduced into the initially introduced ester at the base of the reaction vessel.

The dichloroethane eliminated during the reaction, which distils off at the reaction temperature produced and, with increasing conversion, carries thionyl chloride out of the reaction vessel, is preferably condensed and recycled. Through the circulation thus produced of unreacted thionyl chloride, the latter is utilized in an optimum fashion.

The reaction can also be carried out in the presence of an inert solvent. Examples which may be mentioned are: chlorobenzene, dichlorobenzene or hydrocarbons. This reaction is also preferably carried out at 80° to 130° C.

The end of the reaction can be recognized from the evolution of $SO_2$ and HCl ceasing.

For work-up of the reaction mixture, the dichloroethane produced and, if appropriate, the unreacted thionyl chloride are removed by distillation. The 2-chloroethanephosphonic dichloride formed can be purified by distillation.

The following examples are intended to illustrate the invention. The starting material used was crude bis-2-chloroethyl 2-chloroethanephosphonate, as obtained on Arbusov rearrangement of tris-2-chloroethyl phosphite $P(OCH_2CH_2Cl)_3$ (German Offenlegungsschrift No. 2,132,962; Houben-Weyl, Volume XII/1 (1963), page 389) by heating to 140° C. About 55% of the crude ester was bis-2-chloroethyl 2-chloroethanephosphonate

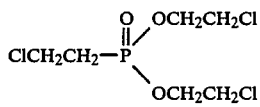

and about 38% was mono(bis-2-chloroethyl 2-chloroethanephosphonate) mono-2-chloroethyl 2-chloroethanephosphonate

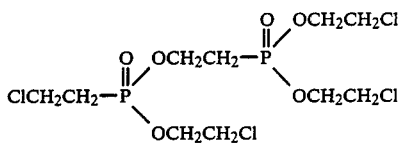

All initial charges and yields relate to the pure content of 93%.

EXAMPLE 1

100 g of crude bis-chloroethyl 2-chloroethanephosphonate and 99.4 g (0.835 mol) of thionyl chloride were heated to 125° C. within 30 minutes in the presence of 1 g of tris-(4-methoxyphenyl) phosphine, vigorous evolution of gas setting in from 90° C. Eliminated dichloroethane and unreacted thionyl chloride distilled via a column into a receiver and were fed back into the reaction mixture via a dip tube at the base of the reaction vessel. The mixture was heated for a further 6 hours at 125° C., with constant feeding-back of unreacted thionyl chloride, and the volatile components were then removed from the reaction mixture by distillation, initially at atmospheric pressure and then at 150-250 mbar and 50°-70° C. 68.4 g of distillate, still containing 25% by weight of unreacted thionyl chloride, were obtained. 52.3 g (79% of theory) of a colorless liquid, of which 93% by weight comprised 2-chloroethanephosphonic dichloride and 7% by weight comprised vinylphosphonic dichloride, were subsequently obtained as the main fraction at 4–5 mbar and 72°–83° C.

EXAMPLE 2

Analogously to Example 1, 150 g of crude bis-chloroethyl 2-chloroethane phosphonate and 149.1 g (1.25 mol) of thionyl chloride were heated to 125° C. within 20 minutes in the presence of 2 g of LiBr, and the reaction mixture was kept at this temperature for 10 hours. During this time, the mixture of thionyl chloride and dichloroethane removed by distillation was continuously fed back in the circuit via a dip tube at the base of the reaction vessel. On distillative work-up, as described in Example 1, 109.8 g of a preliminary fraction, comprising 94.8 g of dichloroethane and 15.0 g of thionyl chloride, were obtained. As the main fraction, 86.6 g (86% of theory) of 2-chloroethanephosphonic dichloride and vinylphosphonic dichloride passed over in the weight ratio 95:5.

COMPARISON EXAMPLE (WITHOUT CATALYST)

Analogously to Example 1, 100 g of crude bis-chloroethyl 2-chloroethanephosphonate and 99.4 g (0.835 mol) of thionyl chloride were heated to 125° C. within 30 minutes, but now in the absence of a catalyst. The mixture was stirred at 125° C. for 5 hours, with constant recycling, via a dip tube at the base of the reaction vessel, of the mixture of thionyl chloride and dichloroethane removed by distillation. Subsequent distillation gave 83.6 g of a preliminary fraction, of which 92% by weight was unreacted thionyl chloride and only 8% by weight was eliminated dichloroethane. A further distillation of the insufficiently reacted reaction mixture was omitted.

EXAMPLES 3–10

Crude bis-chloroethyl 2-chloroethanephosphonate was converted by the procedure of Example 1 in the presence of various catalysts (in each case 1% by weight). The following table shows the catalysts, the reaction temperature, the reaction time, the conversion (relative to thionyl chloride), the yield and the 2-chloroethanephosphonic dichloride to vinylphosphonic dichloride weight ratio (CPC:VPC) in the reaction product:

| Example | Catalyst | Temperature (°C.) | Time (h) | Conversion of $SOCl_2$ (%) | Yield (%) | CPC/VPC |
|---|---|---|---|---|---|---|
| 3 | triphenyl phosphine | 115 | 5 | 82 | 85 | 96:4 |
| 4 | tris-(4-fluorophenyl) phosphine | 115 | 5 | 77 | 53 | 98:2 |
| 5 | tris-(p-tolyl) phosphine | 125 | 6 | 86 | 79 | 89:11 |
| 6 | bis-(4-methoxyphenyl)methyl phosphine | 125 | 6 | 55 | 30 | 96:5 |
| 7 | (N,N—diethyl)aminomethyldiphenyl phosphine | 125 | 7 | 63 | 33 | 96:5 |
| 8 | tributyl phosphine | 125 | 5 | 85 | 66 | 96:5 |
| 9 | tetrabutylammonium bromide | 125 | 6 | 87 | 80 | 93:7 |
| 10 | tetrabutylphosphonium bromide | 127 | 4 | 92 | 81 | 90:10 |

EXAMPLE 11

A 1 liter flask equipped with fractionation attachments, dropping funnel and internal thermometer was flushed with nitrogen. 500 g of crude bis-(2-chloroethyl) 2-chloroethanephosphonate from Arbusov rearrangement of tris-(2-chloroethyl) phosphite and 5 g of triphenyl phosphine were introduced into the flask. The dropping funnel was charged with 530 g (325 ml) of thionyl chloride. 100 ml of thionyl chloride were then run into the base of the reaction vessel, and the mixture was heated to reflux. After 3 hours, the initially vigorous gas evolution was complete; the reaction mixture boiled at a constant bottom temperature of 115° C.

The mixture was cooled to 50° C., and dichloroethane was removed by distillation at 270 mbar to a bottom temperature of 115° C. 125.3 g of distillate were obtained.

After flushing with nitrogen, a further 125 ml of thionyl chloride were added, and the mixture was refluxed for 4 hours. Dichloroethane was again removed by distillation at 270 mbar to a bottom temperature of 115° C.

The remaining 100 ml of thionyl chloride were then added, and the mixture was refluxed for 7 hours. Towards the end of the reaction, a total of 30 ml of dichloroethane were added in portions so that the bottom temperature did not exceed 115° C.

The volatile components were removed by distillation at 270 mbar to a bottom temperature of 115° C. The residue was fractionated at 20 mbar. The fraction passing over at 60°–95° C. was collected. 331.2 g of distillate of the following composition were obtained:

92.2% by weight of 2-chloroethanephosphonic dichloride 3.6% by weight of vinylphosphonic dichloride 1.3% by weight of phosphorus oxychloride.

In addition, 26.6 g of bottoms were produced.

EXAMPLE 12

120 kg of crude bis-(2-chloroethyl) 2-chloroethanephosphonate and 1.2 kg of triphenyl phosphine were placed in a 140 liter enamel stirred reactor with brine-cooled reflux condenser (0° C.). 39.1 kg of thionyl chloride were then introduced at the base of the reactor, and the mixture was heated to reflux. After 4 hours, an internal temperature of 112° C. had been produced; gas evolution was complete. Dichloroethane was removed by distillation at 270 mbar to a bottom temperature of 113° C.; 32.5 kg of dichloroethane were produced.

A further 49.0 kg of thionyl chloride were then introduced as above, and the mixture was refluxed for 5 hours. After removing the dichloroethane by distillation (28.1 kg) at 270 mbar to a bottom temperature of 110° C., 39.1 kg of thionyl chloride were again introduced as above, and the mixture was refluxed for 8 hours. Dichloroethane was then removed by distillation to a bottom temperature of 118° C. 91 kg of crude 2-chloroethanephosphonic dichloride remained as the residue.

We claim:

1. A process for the preparation of 2-chloroethanephosphonic dichloride through reaction of a 2-chloroethanephosphonate of the formula

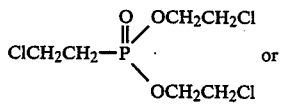

or

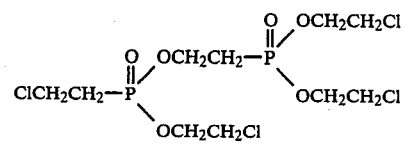

or a mixture of the two esters, with thionyl chloride at a temperature of 60° to 160° C., wherein the reaction is carried out in the presence of a catalyst which contains at least one of the following substances:

(a) tertiary phosphines of the formula

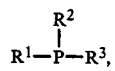

in which the radicals $R^1$, $R^2$ and $R^3$ may be identical or different and denote straight-chain or branched $C_1$–$C_{10}$-alkyl, optionally substituted by $C_1$–$C_4$-alkoxy, $C_1$–$C_4$-alkylthio or $C_1$–$C_4$-dialkylamino radicals, or denote phenyl, optionally substituted by halogen, $C_1$–$C_4$-alkyl or $C_1$–$C_4$-alkoxy radicals, (b) quaternary ammonium or phosphonium salts of the formula

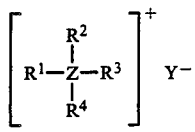

where Z=N or P, where Y⁻ is an anion of a strong acid and in which $R^1$, $R^2$ and $R^3$ have the meaning mentioned in the case of (a) and $R^4$ denotes straight-chain or branched $C_1$-$C_{10}$-alkyl or benzyl which is substituted by halogen, $C_1$-$C_4$-alkyl or $C_1$-$C_4$-alkoxy radicals, (c) alkali metal or alkaline-earth metal halides.

2. The process as claimed in claim 1, wherein a catalyst is employed which contains at least one of the substances mentioned under (a) or (c).

3. The process as claimed in claim 1, wherein the catalyst employed is triphenyl phosphine or lithium bromide.

4. The process as claimed in claim 1, wherein the dichloroethane eliminated and distilled off during the reaction is condensed and recycled.

5. The process as claimed in claim 1, wherein the thionyl chloride is introduced into the initially introduced ester.

6. The process as claimed in claim 1, wherein the thionyl chloride is introduced into the initially introduced ester at the base of the reaction vessel.

7. A process for the preparation of 2-chloroethane-phosphonic dichloride through reaction of a 2-chloroethanephosphonate of the formula

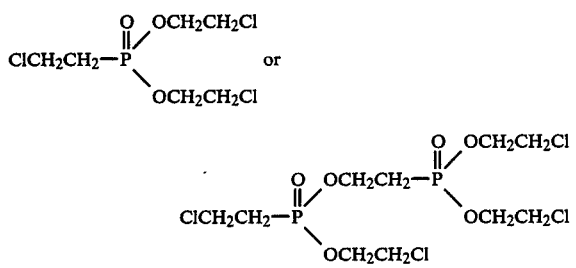

or a mixture of the two esters, with thionyl chloride at a temperature of 60° to 160° C., wherein the reaction is carried out in the presence of a catalyst which contains at least one of the following substances:

(a) tertiary phosphines of the formula

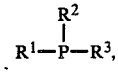

in which the radicals $R^1$, $R^2$ and $R^3$ may be identical or different and denote straight-chain or branched $C_1$-$C_{10}$-alkyl, optionally substituted by $C_1$-$C_4$-alkoxy, $C_1$-$C_4$-alkylthio or $C_1$-$C_4$-dialkylamino radicals, or denote phenyl, optionally substituted by halogen, $C_1$-$C_4$-alkyl or $C_1$-$C_4$-alkoxy radicals, with the exception of those tertiary phosphines, in which all the radicals $R^1$, $R^2$, $R^3$ are unsubstituted alkyl or aryl groups having 1 to 8 C-atoms (b) quaternary ammonium or phosphonium salts of the formula

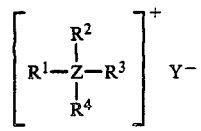

where Z=N or P, where Y⁻ is an anion of a strong acid and in which $R^1$, $R^2$ and $R^3$ have the meaning mentioned in the case of (a) and $R^4$ denotes straight-chain or branched $C_1$-$C_{10}$-alkyl, or benzyl which is substituted by halogen, $C_1$-$C_4$-alkyl or $C_1$-$C_4$-alkoxy radicals, with the exception of those phosphonium chlorides or bromides, in which all the radicals $R^1$, $R^2$, $R^3$, $R^4$ are unsubstituted alkyl or aryl groups having 1 to 8 C-atoms, (c) alkali metal or alkaline-earth metal halides.

8. A process for the preparation of 2-chloroethane-phosphonic dichloride through reaction of a 2-chloroethanephosphonate of the formula

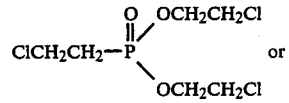

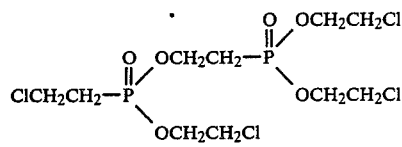

or a mixture of the two esters, with thionyl chloride at a temperature of 60° to 160° C., wherein the reaction is carried out in the presence of a catalyst which contains at least one of the following substances:

I. quaternary ammonium salts of the formula

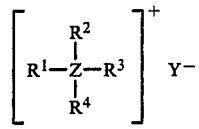

where Y⁻ is an anion of a strong acid and where the radicals $R^1$, $R^2$ and $R^3$ may be identical or different and denote straight-chain or branched $C_1$-$C_{10}$-alkyl, optionally substituted by $C_1$-$C_4$-alkoxy, $C_1$-$C_4$-alkylthio or $C_1$-$C_4$-dialkylamino radicals, or denote phenyl, optionally substituted by halogen, $C_1$-$C_4$-alkyl or $C_1$-$C_4$-alkoxy radicals, and $R^4$ denotes straight-chain or branched $C_1$-$C_{10}$-alkyl, or benzyl which is substituted by halogen, $C_1$-$C_4$-alkyl or $C_1$-$C_4$-alkoxy radicals, II. alkali metal or alkaline-earth metal halides.

* * * * *